United States Patent [19]

Chen et al.

[11] Patent Number: 5,120,899

[45] Date of Patent: Jun. 9, 1992

[54] DIAMONDOID RECOVERY FROM NATURAL GAS FIELDS

[75] Inventors: Catherine S. H. Chen, Berkely Heights; Steven E. Wentzek, Pennington, both of N.J.

[73] Assignee: Mobil Oil Corporation, Fairfax, Va.

[21] Appl. No.: 664,004

[22] Filed: Mar. 4, 1991

[51] Int. Cl.$^5$ .............................. C07C 7/10
[52] U.S. Cl. ................. 585/803; 585/352; 585/867; 208/337; 208/341
[58] Field of Search ............... 585/803, 352, 867; 208/337, 341

[56] References Cited

U.S. PATENT DOCUMENTS

| | | | |
|---|---|---|---|
| 3,676,521 | 7/1972 | Stearns et al. | 260/683.1 |
| 3,737,477 | 6/1973 | Stearns et al. | 260/683.15 |
| 3,851,011 | 11/1974 | Stearns et al. | 260/683.15 |
| 3,923,919 | 12/1975 | Stearns et al. | 260/683.1 |
| 4,182,922 | 1/1980 | Schick et al. | 585/18 |
| 4,239,927 | 12/1980 | Brennan et al. | 585/24 |
| 4,463,201 | 7/1984 | Schick et al. | 585/10 |
| 4,520,221 | 5/1985 | Hsia Chen | 585/517 |
| 4,547,613 | 10/1985 | Garwood et al. | 585/533 |
| 4,827,064 | 5/1989 | Wu | 585/10 |
| 4,827,073 | 5/1989 | Wu | 585/530 |
| 4,912,272 | 3/1990 | Wu | 585/10 |
| 4,952,747 | 8/1990 | Alexander et al. | 585/803 |
| 4,952,748 | 8/1990 | Alexander et al. | 585/803 |
| 4,952,749 | 8/1990 | Alexander et al. | 585/803 |
| 4,967,032 | 10/1990 | Ho et al. | 585/255 |
| 4,982,049 | 1/1991 | Alexander et al. | 585/803 |
| 5,019,665 | 5/1991 | Partridge et al. | 585/803 |

*Primary Examiner*—Asok Pal
*Attorney, Agent, or Firm*—Alexander J. McKillop; Charles J. Speciale; Robert B. Furr, Jr.

[57] ABSTRACT

A process is disclosed for separating diamondoid compounds from a natural gas stream containing the same comprising the steps of contacting the natural gas stream with a selected solvent and fractionating the sorbed diamondoids from the diamondoid-enriched solvent in a vacuum separation stage in the absence of reflux. Polyalphaolefin solvents are preferred, and polyalphaolefin solvents enriched in $C_{30}$ oligomers are more preferred.

15 Claims, 4 Drawing Sheets

5,120,899

DIAMONDOID RECOVERY FROM NATURAL GAS FIELDS

FIELD OF THE INVENTION

The present invention relates to a method for recovering diamondoid compounds from a gas stream containing the same by contacting the gas stream with a selected solvent. The invention further provides a process for continuously having diamondoids dissolved therein and for purifying the diamondoid-enriched solvent produced in the diamondoid recovery process to provide a concentrated diamondoid fraction and a lean solvent suitable for recycle in a continuous sorption process.

BACKGROUND OF THE INVENTION

Many hydrocarbonaceous mineral streams contain some small proportion of diamondoid compounds. These high boiling, saturated, three-dimensional polycyclic organics are illustrated by adamantane, diamantane, triamantane and various side chain substituted homologues, particularly the methyl derivatives. These compounds have high melting points and high vapor pressures for their molecular weights and have recently been found to cause problems during production and refining of hydrocarbonaceous minerals, particularly natural gas, by condensing out and solidifying, thereby clogging pipes and other pieces of equipment. For a survey of the chemistry of diamondoid compounds, see Fort, Jr., Raymond C., *The Chemistry of Diamond Molecules*, Marcel Dekker, 1976.

In recent times, new sources of hydrocarbon minerals have been brought into production which, for some unknown reason, have substantially larger concentrations of diamondoid compounds. Whereas in the past, the amount of diamondoid compounds has been too small to cause operational problems such as production cooler plugging, now these compounds represent both a larger problem and a larger opportunity. The presence of diamondoid compounds in natural gas has been found to cause plugging in the process equipment requiring costly maintenance downtime to remove. On the other hand, these very compounds which can deleteriously affect the profitability of natural gas production are themselves valuable products.

The problem of diamondoid deposition and plugging in natural gas production equipment has been successfully addressed by a controlled solvent injection process. U.S. Pat. No. 4,952,748 to Alexander and Knight teaches the process for extracting diamondoid compounds from a hydrocarbon gas stream by contacting the diamondoid-laden hydrocarbon gas with a suitable solvent to preferentially dissolve the diamondoid compounds into the solvent. Allowed U.S. Pat. application Ser. No. 489,111, filed Mar. 6, 1990, to Cullick and Roach teaches a method for locating the solvent injection point within the natural gas wellbore.

Further studies have revealed that separation of the diamondoid compounds from the diamondoid-enriched solvent is complicated by the fact that numerous diamondoid compounds boil in a narrow range of temperatures surrounding the boiling range of the most preferred solvents U.S Pat. Nos. 4,952,747, 4,952,749, and 4,982,049 to Alexander et al. teach various methods of concentrating diamondoid compounds in the solvent for, among other reasons, recycling the lean solvent fraction for reuse, and each of these processes produces an enriched solvent stream containing a mixture of diamondoid compounds. While these techniques meet the industrial need for a constant supply of relatively lean solvent for continuous recycle, the diamondoid-enriched streams rejected by these processes are not sufficiently pure to themselves be commercially useful. As mentioned above, conventional distillation of diamondoid-containing solvent mixtures is complicated by the fact that diamondoid compounds exhibit vapor pressures which are unusually high for their molecular weights. Further, the relative volatilities of recovered diamondoid mixtures and commonly used solvents such as diesel fuel tend to converge at elevated temperatures, impeding effective partitioning of solvent and diamondoid compounds. Thus it can clearly be seen that a method for recovering diamondoid compounds in relatively high purity from a diamondoid-containing solvent would be highly desirable.

SUMMARY OF THE INVENTION

In accordance with the invention, it has now been found that diamondoids may be readily recovered from gas stream by contact with one particular class of solvents and that the dissolved diamondoids can be recovered in high purity from such solvents under controlled conditions including relatively low temperature and pressure in the absence of reflux to the separation stage. The behavior of the diamondoid/selected solvent system of the invention is surprising because, among other reasons, more severe separation conditions were found to yield impure product mixtures.

The invention provides, in a first aspect, process for separating diamondoid compounds from a solvent comprising the steps of:

(a) providing a solvent containing at least about 70 weight percent paraffins having at least 30 carbon atoms and less than about 5 weight percent aliphatics having less than about 30 carbon atoms, said solvent having at least one diamondoid compound selected from the group consisting of adamantane, diamantane, triamantane, and their substituted homologs, dissolved therein;

(b) charging said diamondoid-containing solvent of step (a) to a separation stage under subatmospheric pressure and temperature within the range of from about 0 to about 150° C.;

(c) withdrawing a vapor stream enriched in diamondoids from said separation stage of step (b) and condensing said vapor stream at a temperature of from about −80° C. to about ambient in the absence of reflux to said separation stage of step (b).

The invention further provides, in a second aspect, a process for extracting diamondoid compounds from a gas stream comprising the steps of:

(a) providing a gas stream containing a recoverable quantity of diamondoid compounds;

(b) mixing said gas stream containing diamondoid compounds with a solvent containing at least about 70 weight percent paraffins having at least 30 carbon atoms and less than about 5 weight percent aliphatics having less than about 30 carbon atoms, in which solvent diamondoid compounds are at least partially soluble;

(c) controlling the conditions including temperature and pressure of said mixture of step (b) above to maintain at least a portion of said mixture in the liquid phase;

(d) separating said mixture under the controlled conditions of step (c), above, into a vapor stream and a diamondoid-enriched solvent stream;

(e) charging said diamondoid-containing solvent of step (d) to a separation stage under subatmospheric pressure and temperature within the range of from about 0 to about 150° C.;

(f) withdrawing a vapor stream enriched in diamondoids from said separation stage of step (e) and condensing said overhead stream at a temperature of from about $-80°$ C. to about ambient in the absence of reflux to said separation stage of step (e).

The process of the invention may further comprise withdrawing a liquid stream from the separation stage and recycling the withdrawn stream to the gas/liquid solvent mixing step.

DETAILED DESCRIPTION

Figure 1:
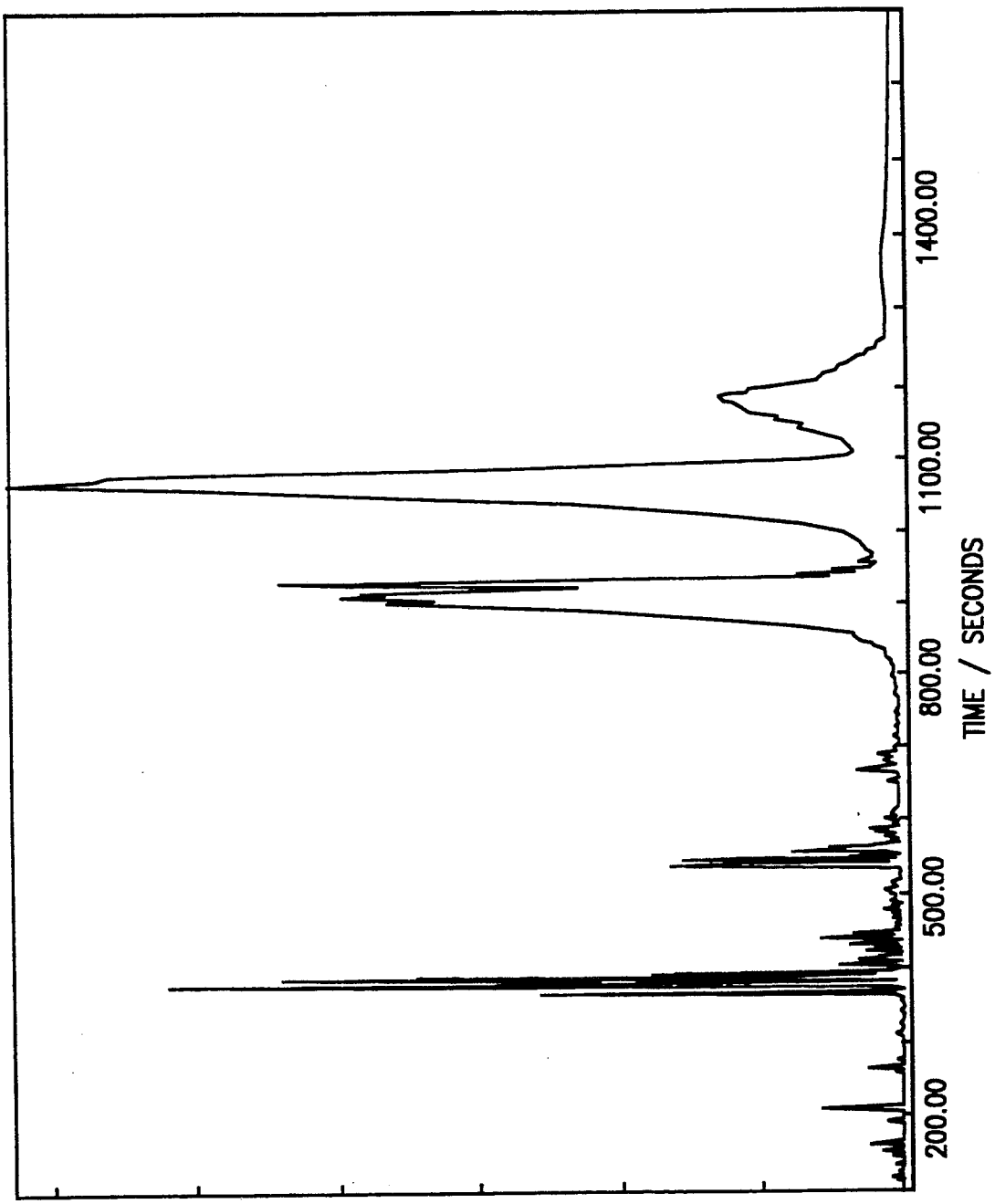
FIG. 1 is a Simdis gas chromatograph of the diamondoid-enriched synthetic polyalphaolefin solvent of Example 1 with the x-axis representing time in units of seconds.
Figure 2:
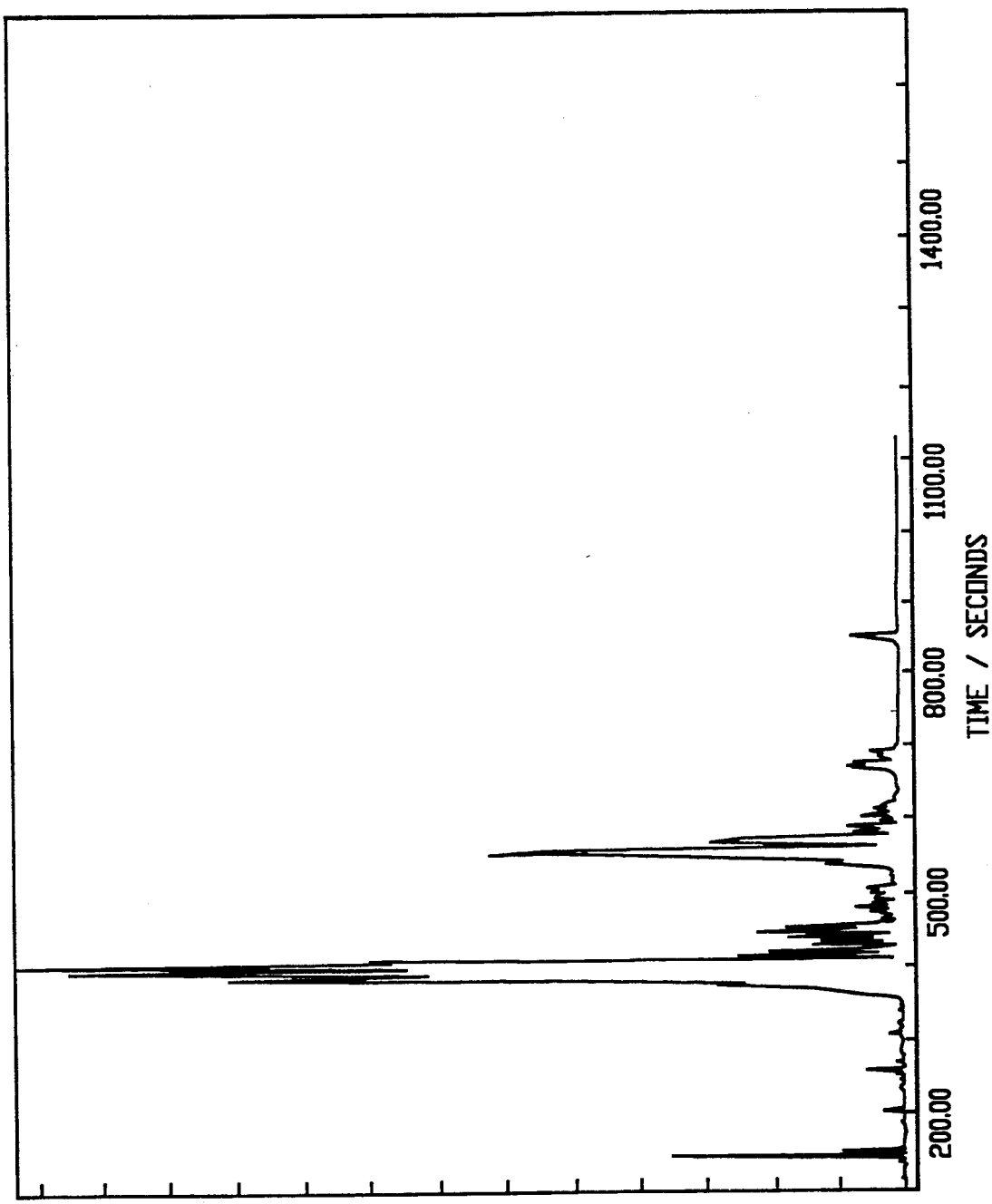
FIG. 2 is a Simdis gas chromatograph of the product derived from Example III.

The term "Simdis" as used herein refers to a standard gas chromatography procedure described in ASTM D 2887-84, which is entitled "Standard Test Method for Boiling Range Distribution of Petroleum Fractions by Gas Chromatography".

Sorption Process Step

The diamondoid sorption step of the present invention contacts a selected solvent with a diamondoid-containing natural gas stream and is carried out in accordance with the teachings of U.S. Pat. No. 4,952,748 to Alexander and Knight.

Solvent selection is critical to achieving the high purity diamondoid product in the subsequent separation step of the invention. Specifically, the solvent must having a boiling range of from about 343° C. (650° F.) to about 649° C. (1200° F.), preferably from about 398° C. (750° F.) to about 649° C. (1200° F.), all measured at atmospheric pressure. Preferred solvents contain less than about 5 weight percent of hydrocarbons having less than 30 carbon atoms and at least about 20 weight percent of hydrocarbons having more than 50 carbon atoms. Because synthetic polyalphaolefins remain liquid over a broad range of temperatures, and are flowable at extremely low temperatures while boiling at relatively high temperatures, they are preferred as solvents. Examples of such preferred polyalphaolefins include those derived from 1-decene, such as polyalphaolefin having from about 30 to about 50 carbon atoms and a branch ratio of less than about 0.19, although the branch ratio of the polyalphaolefin is not considered to be critical in the present method.

The following references are representative of the art of lubricant-grade synthetic oligomers, and are incorporated herein by reference for details of polyalphaolefin synthesis and properties.

U.S. Pat. Nos. 3,676,521, 3,737,477, 3,851,011, and 3,923,919 to Stearns et al. teach lubricants having high Viscosity Index, low pour point, and high stability which comprise ethylene-propylene copolymers produced from monoolefin mixtures containing ethylene and propylene over catalysts including vanadium-aluminum or titanium-aluminum Ziegler-type catalyst systems.

U.S Pat. No. 4,182,922 to Schick et al. teaches a synthetic hydrocarbon oil and a method of making the same involving the copolymerization of propylene or propylene plus higher olefins with small amounts of ethylene.

U.S. Pat. No. 4,239,927 to Brennan et al. relates to a process for producing synthetic hydrocarbon oils by the polymerization of olefins using an aluminum halide catalyst. More specifically, the reference provides a method for preventing accumulation of certain organic halides which were found to be corrosive to process equipment by reacting such organic halides with aromatic hydrocarbons to evolve an alkylation product.

U.S. Pat. No. 4,463,201 to Schick et al. discloses a process for producing high quality synthetic lubricating oils by the copolymerization of ethylene, propylene, and a third 1-olefin, and subsequently dewaxed via a urea adduction process.

U.S. Pat. No. 4,520,221 to Chen teaches a process for producing high Viscosity Index lubricants from light olefins over a catalyst having the structure of ZSM-5, the surface acidity of which has been inactivated by treatment with a suitable base material.

U.S. Pat. No. 4,547,613 to Garwood et al. teaches the conversion of olefin-rich hydrocarbon streams such as ethylene and containing up to about 16 carbon atoms to high Viscosity Index lubricant base stocks by contacting the olefins with a catalyst having the structure of ZSM-5 under elevated pressure.

U.S. Pat. No. 4,912,272 to Wu relates to lubricant mixtures having unexpectedly high viscosity indices. More specifically, the lubricant mixtures comprise blends of high Viscosity Index polyalphaolefins prepared with activated chromium on silica, polyalphaolefins prepared with $BF_3$, aluminum chloride, or Ziegler-type catalysts.

Polyalphaolefins derived from the oligomerization of 1-alkenes, especially 1-decene, which are characterized by high VI (Viscosity Index) and commonly referred to in the art as HVI-PAO lubricant stocks, are particularly preferred as solvents in the present invention. For a discussion of syntheses and properties of HVI-PAO materials, see U.S. Pat. Nos. 4,827,064 to Wu, 4,827,073 to Wu, and 4,967,032 to Ho and Wu, which are incorporated by reference as if set forth at length herein.

The diamondoid-containing natural gas stream may contain other constituents which require circulation of antifouling or corrosion inhibiting additives through the natural gas processing equipment. Many of these additives, as well as certain sulfur-bearing compounds which may be present in the produced natural gas stream require a polar solvent, for example, an ester. Thus the solvent used in the present invention may optionally include at least one polar compound, for example, an organic ester having a boiling point above about 400° C. (750° F.). Suitable organic esters include synthetic lubricant stocks such as dibasic acid esters, polyol esters, polyglycols, and phosphate esters, as disclosed in 12 *Kirk Othmer Encyclopedia of Chemical Technology*, 718, Third Edition (1980).

Distillation Process Step

By selection of the solvent in accordance with the present disclosure, the diamondoid-enriched solvent derived from the gas/solvent contacting step may be readily separated in accordance with the following procedure to provide an essentially pure diamondoid product stream.

The diamondoid-enriched solvent is charged to a separation stage under vacuum conditions ranging from about 0.05 to about 25 Torr, preferably from about 0.1 to about 10 Torr, most preferably from about 0.2 to about 2 Torr. The separation stage is suitably contained in a vessel rated for full vacuum service under the operating temperature selected from the range of about 0° C. to about 150° C. The separation is preferably connected to a receiver by heated lines of relatively large diameter to avoid condensation or sublimation of valuable products before the products reach the receiver. The separation step may be conducted in batch or continuous mode, however, it is most preferred to purify a batch of diamondoid-enriched solvent collected from the sorption stage via a slipstream. The diamondoid-enriched solvent from the sorption stage is then returned to the sorption stage for reuse, and the diamondoid compounds collected in the receiver are drained to storage.

The separation vessel may more particularly comprise a flash drum rated for full vacuum service at the solvent endpoint temperature. For example, a vessel equipped with suitable heating means, such as external or internal steam or electric heating coils and a temperature controller would be a useful separation stage apparatus.

To initiate the separation process step in the preferred batch mode, the separation stage is filled with diamondoid-enriched solvent and the temperature is raised incrementally and pressure is decreased until a vapor product flow is detected, at which point the temperature and pressure are held constant until the vapor product flow ceases. The pot temperature is then raised and/or the pressure is decreased to continue separation.

Example

EXAMPLE I

A synthetic liquid hydrocarbon solvent enriched in $C_{30}$ polyaolefins was mixed with a cooled, produced diamondoid-containing natural gas stream to sorb diamondoids from the produced natural gas. The composition of the synthetic hydrocarbon solvent used is summarized below in Table 1. The diamondoid-enriched synthetic hydrocarbon solvent appeared dark in color and contained black solids. After filtering by suction through Celite filter aid, the resulting liquid mixture was separated into aqueous and oil layers. The aqueous layer was condensate from the produced natural gas stream, was yellow, and was discarded. The oil layer, after being dried over anhydrous sodium sulfate, was nearly water white and essentially had the original appearance of the lean synthetic hydrocarbon solvent, but had a distinctly unpleasant odor. This oil layer was analyzed by gas chromatography using a Simdis Column Supelco 2-5323, 5.0 m in length, 0.53 mm ID and 0.5 um film thickness. The resulting gas chromatograph is shown in FIG. 1.

TABLE 1

| Constituent | Weight Percentage |
| --- | --- |
| $C_1$-$C_{29}$ paraffins | ≈5% |
| $C_{30}$ paraffins | ≈35% |
| $C_{40}$ paraffins | ≈45% |
| $C_{50}$ paraffins | ≈15% |

EXAMPLE II

This is a comparative example to illustrate the incomplete separation typically achieved with conventional vacuum distillation of a diamondoid-enriched paraffinic solvent.

One liter of the filtered diamondoid-enriched synthetic hydrocarbon solvent of Example I was distilled under vacuum in an ASTM 2887 still equipped with a heated, packed reflux column. Heated silicone fluid was circulated through the two condensers. Two traps, one at room temperature followed by another a dry ice/acetone temperature were used. The products distilled at all temperature/vacuum combinations used in the following order:

(a) nondiamondoid low boiling liquid;
(b) solid adamantane;
(c) liquid adamantane derivatives;
(d) solid diamantane; and
(e) a small amount of triamantane.

The following were observed:

(1) Except for fraction (a), each fraction was contaminated by significant quantities of other fractions.

(2) Adamantane and diamantane sublimed over causing plugging of the condensers, although the condensers were heated requiring physical removal of the accumulated solids. Some adamantane also was observed to condense first in the room temperature trap, then resublimed from the room temperature trap to the dry ice trap.

(3) Triamantane was reluctant to distill, and most of the triamantane present in the original mixture remained in the pot or the lower part of the column even when the pot was at 260° C. and at a vacuum of 2.3 Torr. None of the distilled fractions were contaminated with the paraffinic solvent. Three distillations were performed, with each distillation requiring about 10 hours.

After each distillation, the column and condensers were extracted of the retained products by refluxing with hexane. The products recovered from the hexane washings, were mainly diamantane and triamantane with about an equal amount of the paraffinic solvent which was present in the refluxing column. More than 50% of the triamantane remained in the pot residue with the paraffinic solvent. The products recovered from the hexane washings, mainly diamantane and triamantane, also contained about 50% of the paraffinic solvent.

EXAMPLE III

In Example III, the diamondoid constituents were separated from the paraffinic solvent using short-path separation in a Kugelrohr apparatus under a vacuum of 0.3 Torr using only one receiver. The Kugelrohr apparatus used was purchased from the Aldrich Company, 1001 West Saint Paul Avenue, Milwaukee, WI, 53223. A Kugelrohr apparatus shown in the 1990 Aldrich catalog on page 1859. With the receiver immersed in dry ice/acetone, diamantane and triamantane were sublimed cleanly and rapidly as they were removed from the paraffinic solvent at a pot temperature as low as 125° C. The paraffinic solvent was carried over at pot temperatures of about 140° C. Three sets of this separation were performed corresponding to the three distillations performed in Example II. Each separation required from about 1 to about 2 hours.

Based on the yield of each separation, the filtered diamondoid-containing synthetic hydrocarbon of Example I was determined to contain from about 9.2 to about 9.4% diamondoids based on weight of diamondoids recovered. The recovered diamondoids were principally liquid at room temperature and were water white. The separated paraffinic solvent was brown in color due to prolonged heating during the distillation described in Example II.

EXAMPLE IV

This example illustrates a direct and rapid separation technique which produces sharply defined fractions of high purity. The filtered diamondoid-containing polyalphaolefin solvent of Example I was used as a starting material in Example IV.

Two consecutive receivers were used in Example IV in contrast to the single receiver used in Example III, because the mixture contained more volatile adamantanes as well as the less volatile diamantanes and triamantanes. The separation started at 0.1–0.3 Torr vacuum at room temperature. The pot temperature was increased in 25° C. increments. White solids/liquid distilled noticeably at a pot temperature of 75° C. The temperature was held constant until no more material distilled off. The temperature was then further increased in the same manner to 125° C. and the separation was continued until no more material distilled off. The separation took approximately 2 hours, and the recovered diamondoids comprised 9.2% by weight of the original diamondoid-enriched polyalphaolefin solvent mixture. The residual polyalphaolefin solvent mixture was water white, and was characterized by the gas chromatograph shown in FIG. 3. The residual polyalphaolefin solvent was suitable for reuse in sorbing diamondoids from hydrocarbon gas streams.

EXAMPLE V

Example V illustrates a preferred process for the efficient recovery of diamondoids from a hydrocarbon gas stream.

The synthetic polyalphaolefin solvent of Examples I–IV, above, was found to exist as a homogeneous liquid mixture with diamondoid concentrations as high as 60% diamondoids and 40% paraffinic solvent, by weight at room temperature. The experimental procedure of Example 1 was therefore repeated at 6 times the contact time used in Example 1. The raw sample was filtered in accordance with the procedure of Example I and the filtered diamondoid-enriched solvent was separated using the technique of Example IV. The separation of diamondoids from the synthetic polyalphaolefin solvent was found to be essentially clean, with the distilled diamondoids being essentially free of solvent. Essentially all of the diamondoids originally contained in the diamondoid-enriched polyalphaolefin solvent were recovered.

EXAMPLE VI

Example VI illustrates operation of the inventive diamondoid recovery process in a producing natural gas field operation.

The method of U.S. Pat. No. 4,952,748 to Knight and Alexander is conducted to sorb diamondoid compounds from a natural gas stream into a solvent. The particular solvent employed contains less than 5% by weight of hydrocarbons halving less than 10 carbon atoms and more than 95% by weight of hydrocarbons containing more than 30 carbon atoms. When the diamondoid concentration in the solvent reaches approximately 60% by weight of the total mixture, the diamondoids are recovered by the diamondoid/solvent as taught in Examples I–III. The cycle is repeated continuously and additional fresh solvent is added as required.

Changes and modifications in the specifically described embodiments can be carried out without departing from the scope of the invention which is intended to be limited only by the scope of the appended claims.

What is claimed is:

1. A process for separating diamondoid compounds from a solvent comprising the steps of:
    (a) providing a hydrocarbon solvent containing at least about 70 weight percent paraffins having at least 30 carbon atoms and less than about 5 weight percent aliphatics having less than about 30 carbon atoms, said solvent having at least one diamondoid compound selected from the group consisting of adamantane, diamantane, triamantane, and their substituted homologs, dissolved therein;
    (b) charging said diamondoid-containing hydrocarbon solvent of step (a) to a separation stage under subatomspheric pressure and temperature within the range of from about 0 to about 150° C.; and
    (c) withdrawing a vapor stream enriched in diamondoids from said separation stage of step (b) and condensing said vapor stream at a temperature from about $-80°$ C. to about ambient in the absence of reflux to said separation stage of step (b).

2. The process of claim 1 wherein said hydrocarbon solvent comprises the polymerization product of an alpha-olefin.

3. The process of claim 2 wherein said polyalphaolefin solvent is enriched in $C_{30}$ and $C_{40}$ hydrocarbons.

Figure 3:
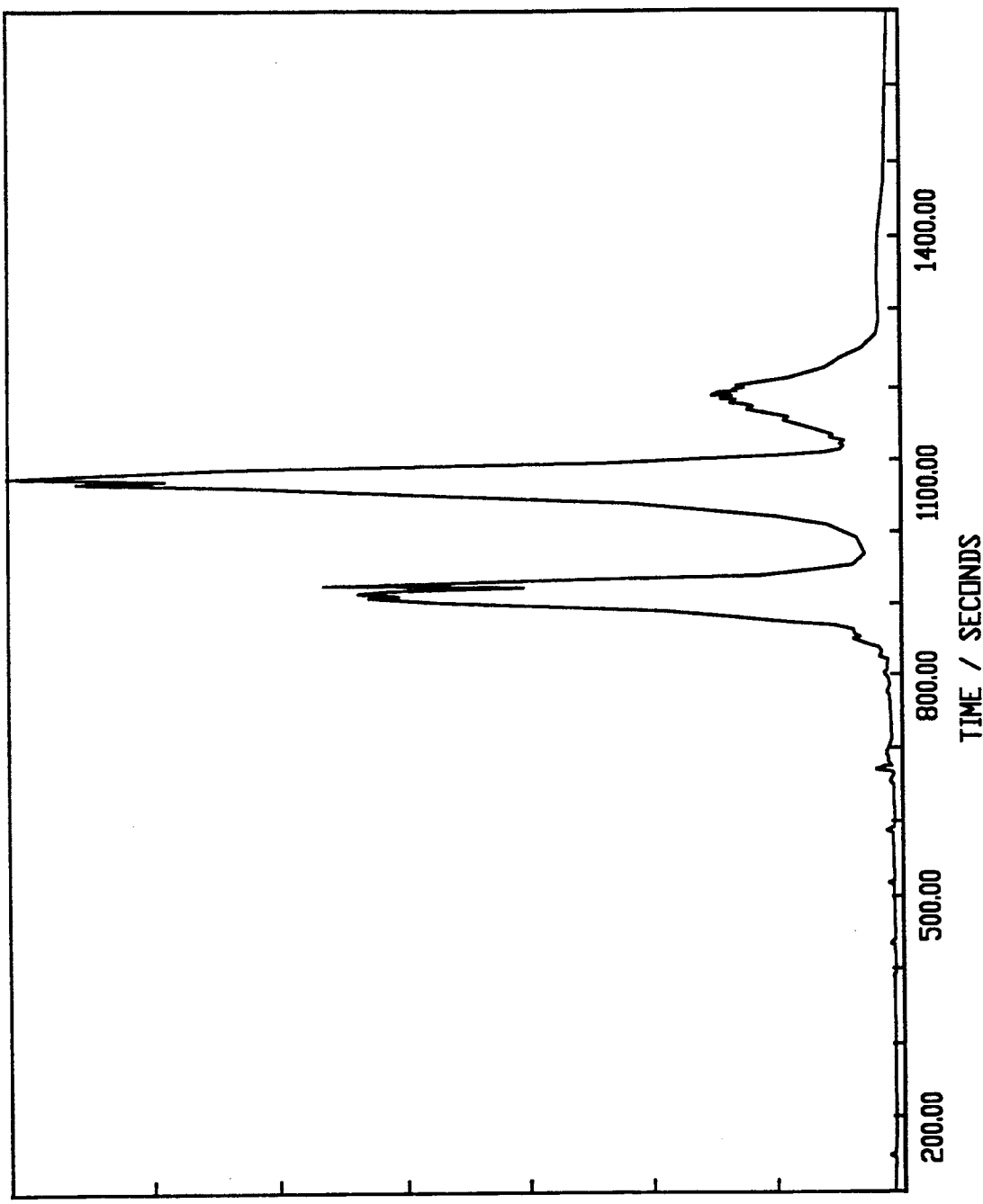
FIG. 3 is a Simdis gas chromatograph of the residual synthetic polyalphaolefin from Example III.

4. The process of claim 1 wherein said solvent is characterized by a Simdis chromatograph substantially as shown in FIG. 3.

Figure 4:
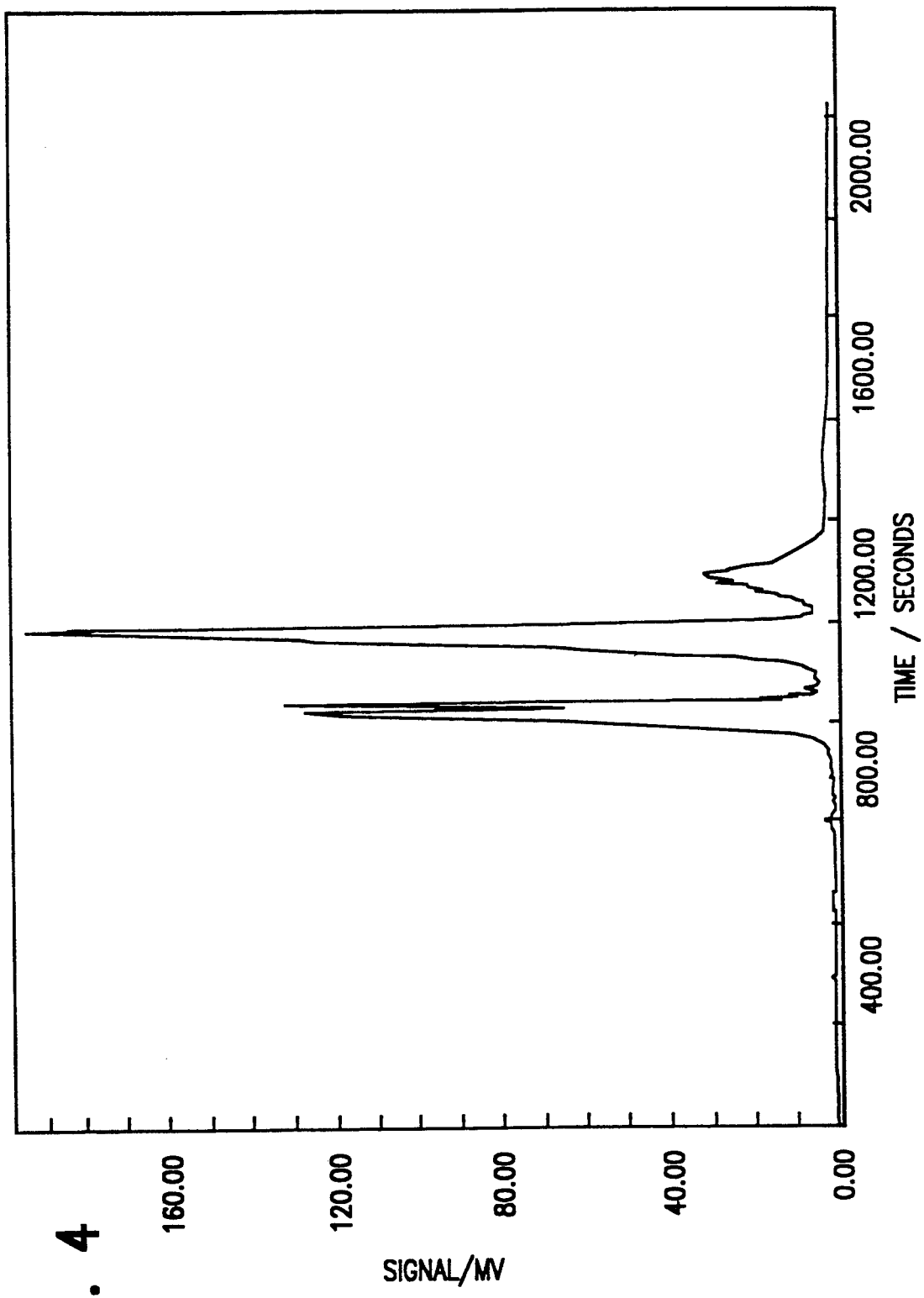
FIG. 4 is a Simdis gas chromatograph of the synthetic polyalphaolefin solvent used in Example IV.

5. The process of claim 1 wherein said solvent is characterized by a Simdis chromatograph substantially as shown in FIG. 4.

6. A process for extracting diamondoid compounds from a gas stream comprising the steps of:
    (a) providing a gas stream containing a recoverable quantity of diamondoid compounds;
    (b) mixing said gas stream containing diamondoid compounds with a hydrocarbon solvent in which diamondoid compounds are at least partially soluble, wherein said hydrocarbon solvent contains at least about 70 weight percent paraffins having at least 30 carbon atoms and less than about 5 weight percent aliphatics having less than about 30 carbon atoms;
    (c) controlling the conditions including temperature and pressure of said mixture of step (b) above to maintain at least a portion of said mixture in the liquid phase;
    (d) separating said mixture under the controlled conditions of step (c), above, into a vapor stream and a diamondoid-enriched solvent stream;
    (e) charging said diamondoid-containing solvent of step (d) to a separation stage under subatmospheric pressure and temperature within the range of from about $-80°$ C. to about ambient;
    (f) withdrawing an vapor stream enriched in diamondoids from said separation stage of step (e) and condensing said overhead stream at a temperature of less than about 150° C. in the absence of reflux to said separation stage of step (e).

7. The process of claim 6 further comprising withdrawin a liquid stream from said separation stage of step (e)

and recycling said withdrawn liquid stream to said mixing step (b).

8. The process of claim 6 wherein said hydrocarbon solvent comprises the polymerization product of an alpha-olefin.

9. The process of claim 7 wherein said polyalphaolefin solvent is enriched in $C_{30}$ and $C_{40}$ hydrocarbons.

10. The process of claim 7 wherein said solvent further least 50 carbon atoms.

11. The process of claim 6 wherein said solvent is characterized by a Simdis chromatograph substantially as shown in FIG. 3.

12. The process of claim 6 wherein said solvent is characterized by a Simdis chromatograph substantially as shown in FIG. 4.

13. The process of claim 6 wherein said solvent further comprises a plar constituent.

14. The process of claim 13 wherein said polar constituent comprises an ester.

15. The process of claim 14 wherein said ester has a boiling point of at least 400° C. at atmospheric pressure.

* * * * *

UNITED STATES PATENT AND TRADEMARK OFFICE
CERTIFICATE OF CORRECTION

PATENT NO. : 5,120,899

DATED : June 9, 1992

INVENTOR(S) : C. S. H. Chen and S. E. Wentzek

It is certified that error appears in the above-identified patent and that said Letters Patent is hereby corrected as shown below:

Column 9:
In Claim 10, line 2, after "further" insert --comprises more than 20 weight percent of hydrocarbons having at--

Column 10:
In Claim 13, line 2, "plar" should be --polar--

Signed and Sealed this

Twenty-first Day of September, 1993

Attest:

BRUCE LEHMAN

*Attesting Officer*     *Commissioner of Patents and Trademarks*